United States Patent [19]

Holt

[11] Patent Number: 4,684,362

[45] Date of Patent: Aug. 4, 1987

[54] METHOD FOR COLLECTING NASAL SECRETIONS

[76] Inventor: James J. Holt, 4004 5th St., NW., Rochester, Minn. 55901

[21] Appl. No.: 242,932

[22] Filed: Mar. 12, 1981

[51] Int. Cl.[4] .................. A61M 31/00; A61M 1/00
[52] U.S. Cl. .................. 604/54; 604/317; 128/765
[58] Field of Search .............. 128/760, 763, 765, 766, 128/250, 276, 277, 278, 280, 281, 282, 297, 298, 299, 300, 765; 604/317, 54

[56] References Cited

U.S. PATENT DOCUMENTS 2,280,992 4/1942 Wright et al. .................. 128/276
3,502,078 3/1970 Hill et al. .................. 128/278

Primary Examiner—C. Fred Rosenbaum
Assistant Examiner—J. L. Kruter
Attorney, Agent, or Firm—Zarley, McKee, Thomte, Voorhees & Sease

[57] ABSTRACT

A method for collecting nasal secretions includes providing a collection apparatus having an elongated collection arm having one end portion adapted for introduction into the nose, a suctioning arm connected to a vacuum source and a collection cup connected to the opposite ends of both arms. Due to the vacuum from the suctioning arm, nasal secretions are drawn from the nose through the collection arm and deposited in the collection cup. The method of the invention includes stimulating the lining of the nose so that an adequate volume of secretions may be collected, then inserting the one end of the collection arm into the nose and causing vacuum to be communicated to the collection arm for drawing nasal secretions therethrough into the collection cup.

11 Claims, 3 Drawing Figures

METHOD FOR COLLECTING NASAL SECRETIONS

BACKGROUND OF THE INVENTION

The present invention is directed generally to a method and apparatus for collecting nasal secretions and more particularly to a method and apparatus for collecting large amounts of uncontaminated, undiluted nasal secretions.

It has been discovered that an examination of human nasal secretions can be very helpful in the diagnosis and treatment of certain nasal disorders. The problem with applying this discovery is that heretofore it has been impossible to easily and consistently collect sufficient quantities of uncontaminated and undiluted nasal secretions.

Known methods for collecting human nasal secretions can be divided into three major categories. The first category and simplest method is to have the patient blow the nose onto paper or glass whereupon the secretions can be collected and placed in a container for subsequent use. This method will not prevent contamination by lacrimal secretions or allow the right-sided secretions to be kept from the left.

The second category entails washing the nasal mucosa and collecting the washings. But all of the various washing methods risk introducing a contaminated solution into the nose. Furthermore, the solution dilutes the nasal secretion and this dilution factor is almost impossible to measure. It is also likely that nasal secretions collected by these washing methods would be contaminated by lacrimal secretions.

The third category of methods for collecting nasal secretions relate to placing an absorptive material in the nose and then recovering the secretions from the absorptive material. This has been done with cotton swabs, filter paper and small cellulose acetate sponges. The problems with these methods include the risk of contamination by the absorbent material and the difficulty of fully recovering all of the components of nasal secretions from the absorbent material.

None of these methods allow the collection of a large volume of nasal secretions that are not contaminated by either lacrimal secretions or the collection apparatus.

Accordingly, a primary object of the invention is to provide an improved apparatus and method for collecting nasal secretions.

Another object is to provide a method and apparatus for collecting large amounts of uncontaminated, undiluted nasal secretions.

Another object is to provide a method and apparatus for collecting nasal secretions which is comfortable for the patient and easily used by an operator.

Another object is to provide an apparatus wherein nasal secretions may be deposited directly into a collection cup without further handling.

Another object is to provide a method and apparatus for collecting nasal secretions without risk of contamination by lacrimal secretions.

Another object is to provide a nasal secretions collecting apparatus which is simple in construction, economical to manufacture and efficient in operation.

These and other objects of the invention will be apparent from the following description.

SUMMARY OF THE INVENTION

The method and apparatus for collecting nasal secretions according to the present invention are particularly adapted for collecting large amounts of uncontaminated, undiluted nasal secretions. The apparatus includes an elongated collection arm having one end adapted for introduction into a nose through an anterior approach, a suctioning arm having one end adapted for connection to a vacuum source and a collection cup. The collection cup is connected to the collection and suctioning arms in airtight relation so that communication is established between the collection arm and suctioning arm for drawing nasal secretions from a nose, through the collection arm, and into the collection cup.

According to the method of the present invention, the lining of a nose is stimulated to produce nasal secretions. The suctioning arm of a suction apparatus is then connected to a source of vacuum and the elongated collection arm is inserted into one side of the nose. A vacuum is communicated to the collection arm from the suctioning arm thereby drawing nasal secretions into the collection arm and depositing said secretions in said collection cup. The nose may be stimulated by inserting a cellulose acetate pledget into the nose for a limited time. A separate collection apparatus and collection cup is preferably used for each side of the nose.

Precleaning of the pledgets prevents contamination from any trace metals in the pledgets themselves and contamination from lacrimal secretions is easily avoided by directing the collection arm away from the inferior meatus of the nose. Accordingly, significant quantities of nasal secretions may be collected without any contamination or dilution factors to be measured.

DESCRIPTION OF THE PREFERRED EMBODIMENTS

Figure 1:
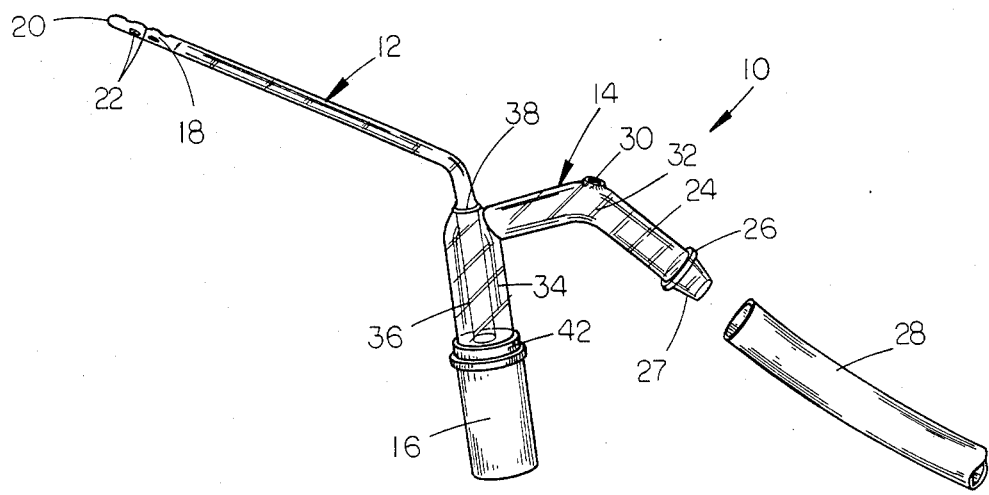
FIG. 1 is a perspective view of the nasal secretions collecting apparatus of the invention.
Figure 2:
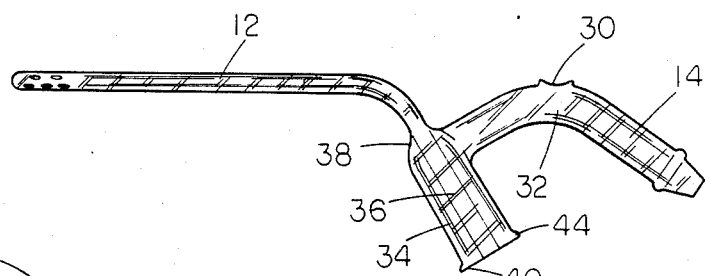
FIG. 2 is a side view of the apparatus, with the collection cup removed.

The collection apparatus 10 of the present invention is shown in FIGS. 1 and 2 as including an elongated collection arm 12, a suctioning arm 14 and a collection cup 16.

The collection arm 12 has one end portion 18 adapted for introduction into a nose through an anterior approach. Whereas collection arm 12 is generally tubular, the terminal end of portion 18 is closed by a generally hemispherical shaped closure wall 20, for example. Nasal secretions are drawn into the tubular arm through a plurality of circumferentially and axially spaced-apart openings 22 through end portion 18.

Suctioning arm 14 has one end 24 adapted for connection to a vacuum source. For example, the exterior peripheral flange 26 cooperates with tapered end portion 27 for insertion of the suctioning arm into the suction hose connected to a wall outlet of a central vacuum system commonly provided in hospitals. Such a hose 28 provides a constant source of vacuum. Alternatively, a collapsible bulb could be attached to the end of suctioning arm 14 to effect a temporary vacuum.

An opening 30 is provided on the top side of an elbow 32 in suctioning arm 14. The opening 30 may be partially or fully closed by a physician's finger when collecting nasal secretions for regulating the application of vacuum from suctioning arm 14 to collection arm 12.

The connection between collection arm 12, suctioning arm 14 and collection cup 16 is such that vacuum is communicated to the collection arm for drawing nasal secretions from a nose, through the collection arm and into the collection cup. It is important that secretions not be drawn into the suctioning arm 14. Accordingly, in the preferred embodiment shown in the drawings, a sleeve 34 encircles the opposite end 36 of collection arm 12 and has an upper end which is sealed onto and around the collection arm as at 38. As seen in FIG. 2, the lower ends of both the collection arm 12 and sleeve 34 terminate in the same plane. The suctioning arm 14 has an opposite end 40 which communicates with sleeve 34 at a position above the opposite end 36 of collection arm 12. Accordingly, when collection cup 16 is secured onto the lower end of sleeve 34 in airtight relation, vacuum is communicated to the collection arm 16 from suctioning arm 14 but any secretions drawn into the collection arm are deposited by gravity into collection cup 16.

Connection of the collection cup 16 onto sleeve 34 is accomplished by a flexible coupling 42 which cooperates with an exterior flange 44.

The method for collecting nasal secretions according to the present invention involves the use of collection apparatus 10. However, it is first desirable to stimulate the nose to produce nasal secretions. The preferred method of stimulation is to insert a cellulose acetate pledget which is commercially available from the Weck-Cell Company, into the nose for a limited period of time. The cellulose acetate material is cut into 4×8 millimeter strips. The sponges are placed in a 2 mM solution of EDTA for twelve hours followed by three sequential rinses in distilled water and then allowed to dry. The pledgets are thereby cleaned to remove any trace metals such as residual zinc so as to avoid contaminating the nose prior to collecting the secretions. The cleaned sponges or pledgets are then stored in a clean polyethylene vial until use. Forceps used in handling the sponges were teflon coated to prevent contamination by metals.

In operation, the patient is first asked to blow the nose. Examination of the nose was conducted under direct vision and any residual crusts were removed with forceps or suction. One cellulose acetate pledget was placed under the nasal bone on each side of the nose. A small piece of paper tape was placed over the upper two-thirds of the nostril. The patient was then instructed to sneeze through the open mouth and was given a towel to clear any tearing or excess nasal drainage. After ten minutes, the tape was removed and the pledgets were taken from the nose and discarded.

Under direct vision with the use of a head mirror and nasal speculum, the long collection arm 12 of the collection apparatus 10 is placed into the nose. Directing the collection arm away from the inferior meatus avoids contamination by lacrimal secretions since the lacrimal duct empties into the inferior meatus of the nose. Repeated aspirations into the nose were usually needed to collect the adequate volume of secretions.

When each collection cup had approximately 1 to 2 cubic centimeters of secretions, the procedure was terminated. The collection cup was then removed, capped, labeled and stored in the freezer at approximately −19°

C. A separate collection apparatus and cup were used for each side of the nose.

Figure 3:
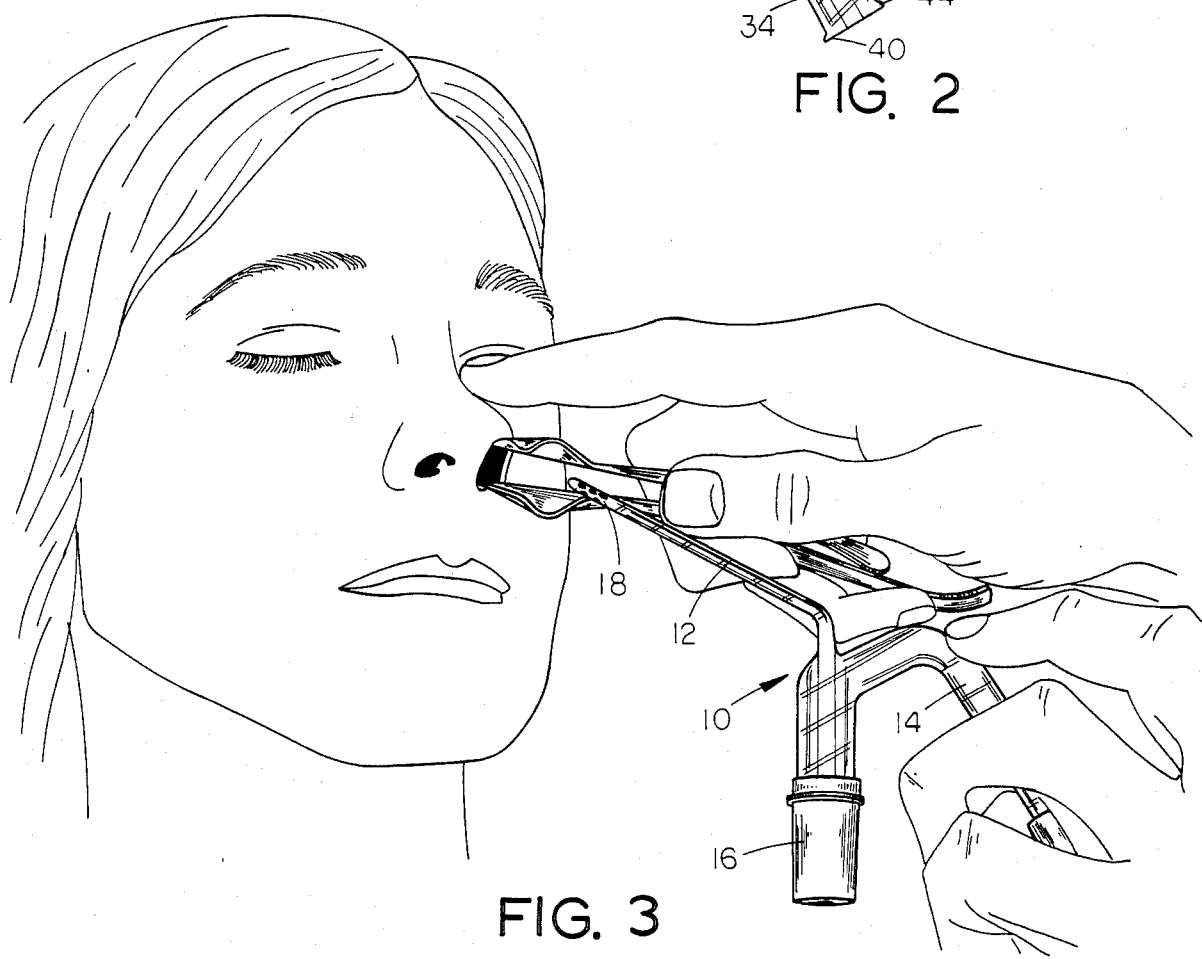
FIG. 3 is an illustration of the apparatus in use for collecting nasal secretions.

The shape of collection apparatus 10 is designed to facilitate insertion of the collection arm into the nose under direct vision as illustrated in FIG. 3. The end portion 24 of suctioning arm 14 is inclined only slightly downwardly from the angle of the longest part of collection arm 12. Sleeve 34 and collection cup 16 are inclined at an obtuse angle relative to the outer straight length of collection arm 12 to avoid contact with the patient's face or chest. The provision of opening 30 on an elbow of the suctioning arm 14 enables a physician to easily open and close the opening with his index finger as shown in FIG. 3 to selectively apply the constant vacuum from hose 28 to the collection arm 12. When the index finger is released, the vacuum primarily just draws air into opening 30.

Whereas specific dimensions are not critical to the present invention, one embodiment has been satisfactorily constructed with a collection arm having an outer straight portion of approximately 9 centimeters, with the opposite bent end portion received within sleeve 34 having a length of approximately 3 centimeters. The collection arm has an outside diameter of 3 millimeters and ten 0.3 millimeter openings 22 spaced approximately 4 millimeters apart. Sleeve 34 has a 12 millimeter outside diameter and suction arm 14 has a 8 millimeter outside diameter. Opening 30 has a 4 millimeter diameter.

The collected nasal secretions are useful for the following analyses: (1) protein, (2) electrolytes, (3) trace metals, (4) enzymes, (5) immuno globulins, (6) eosinophils, (7) cytology, (8) drug levels, (9) antibody levels, (10) antibiotic levels, (11) bacteria count and (12) viral studies.

The method of the invention enables the collection of adequate volumes of secretions with minimal, if any, discomfort for the patient. No medication is used with the pledgets for stimulating the nose and by using the specially constructed apparatus of the invention, one is able to suction in the nose under direct vision, thus reducing discomfort to the patient and avoiding trauma to the nose.

Thus there has been shown and described a method and apparatus for collecting nasal secretions which accomplishes at least all of the stated objects.

I claim:

1. The method of collecting uncontaminated and undiluted nasal secretions from a nose including an inferior meatus, comprising, providing a collection apparatus including an elongated collection arm and a suctioning arm in communication with a collection cup, connecting said suctioning arm to a source of vacuum, inserting one end of said collection arm into the nose, directing the collection arm away from the inferior meatus thereby avoiding contamination by lacrimal secretions, maintaining the nose free of contamination and dilution factors, causing vacuum to be communicated from said suctioning arm to said collection arm, and thereby drawing nasal secretions into said collection arm and depositing said secretions in said collection cup.

2. The method of claim 1 further comprising stimulating the lining of a nose to produce nasal secretions.

3. The method of claim 2 wherein stimulating the lining of a nose comprises inserting a pledget into one side of the nose, leaving said pledget in place for a limited period of time, and removing said pledget.

4. The method of claim 3 wherein said pledget comprises cellulose acetate material.

5. The method of claim 1 further comprising spreading the nasal opening with a nasal speculum while inserting the collection arm.

6. The method of claim 1 further comprising using a separate collection apparatus and collection cup for each side of the nose.

7. The method of claim 1 further comprising regulating the application of vacuum from said suctioning arm to said collection arm.

8. The method of claim 1 further comprising shining a light into the nose whereby the collection arm may be inserted into the nose under direct vision.

9. The method of claim 1 further comprising removing the collection cup from said apparatus, capping the same and saving said cup and the secretions therein for analysis.

10. The method of collecting nasal secretions, comprising, providing a collection apparatus including an elongated collection arm and a suctioning arm in communication with a collection cup, connecting said suctioning arm to a source of vacuum, inserting one end of said collection arm into the nose, causing vacuum to be communicated from said suctioning arm to said collection arm, and thereby drawing nasal secretions into said collection arm and depositing said secretions in said collection cup, stimulating the lining of a nose to produce nasal secretions by inserting a pledget into one side of the nose, leaving said pledget in place for a limited period of time, and removing said pledget, and cleaning said pledgets for removing trace metals prior to insertion into the nose.

11. The method of collecting nasal secretions, comprising, providing a collection apparatus including an elongated collection arm and a suctioning arm in communication with a collection cup, connecting said suctioning arm to a source of vacuum, inserting one end of said collection arm into the nose, causing vacuum to be communicated from said suctioning arm to said collection arm, and thereby drawing nasal secretions into said collection arm and depositing said secretions in said collection cup, removing the collection cup from said apparatus, capping the same and freezing said cup and the secretions therein.

* * * * *